United States Patent [19]

Regnier et al.

[11] Patent Number: 4,599,338
[45] Date of Patent: Jul. 8, 1986

[54] ANTIMIGRAINE 8-[3-(4-AMINOCARBONYL PIPERAZINO AND PIPERIDINO) PROPYL[XANTHINES

[75] Inventors: Gilbert Regnier, Chatenay Malabry; Claude Guillonneau, Clamart; Jacques Duhault, Croissy Sur Seine; Francois Roman, Courbevoie, all of France

[73] Assignee: Adir, S.A.R.L., Neuilly-sur-Seine, France

[21] Appl. No.: 692,049

[22] Filed: Jan. 16, 1985

[30] Foreign Application Priority Data

Jan. 17, 1984 [FR] France .................. 84 00659

[51] Int. Cl.$^4$ ..................... A61K 31/52; C07D 473/06
[52] U.S. Cl. ..................... 514/265; 514/227;
544/118; 544/269; 544/270; 544/271; 544/390;
260/243.3; 546/244
[58] Field of Search ................. 514/265, 227; 544/269,
544/270, 271, 390, 118; 260/243.3; 546/244

[56] References Cited

U.S. PATENT DOCUMENTS

| 4,284,633 | 8/1981 | Friebe ................. 514/265 |
| 4,308,387 | 12/1981 | Bjork ................. 544/390 |
| 4,548,820 | 10/1985 | Regnier et al. ........ 544/269 |

FOREIGN PATENT DOCUMENTS 2116302  8/1978  France .................. 514/265

OTHER PUBLICATIONS

Cygankiewicz, Chemical Abstracts 89: 109376r.
Gorczyca Il Farmaco-Ed. Sc. 29(10) pp. 802-810 (1974).

Primary Examiner—Donald G. Daus
Assistant Examiner—Robert Benson
Attorney, Agent, or Firm—Gordon W. Hueschen

[57] ABSTRACT

Xanthine compounds of the formula:

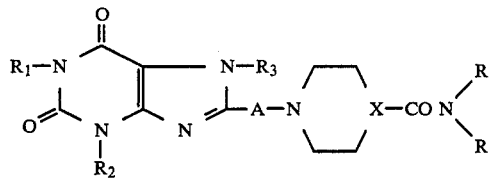

in which:
$R_1$ is hydrogen or ($C_1$–$C_5$) alkyl;
$R_2$ is hydrogen, ($C_1$–$C_5$) alkyl optionally having a double bond, or benzyl;
$R_3$ is hydrogen or methyl;
A is $(CH_2)_n$, in which n is an integer from 1 to 4, optionally substituted, when n is higher than 1, by hydroxy;
X is nitrogen or

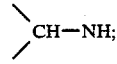

and the substituents R are each ($C_1$–$C_5$) alkyl or they form together a polymethylene chain from $C_4$ to $C_6$, optionally containing an oxygen or a sulfur atom.

These compounds and physiologically tolerable acid addition salts thereof may be used as medicines especially in the treatment of migraine and asthenia.

8 Claims, No Drawings

ANTIMIGRAINE 8-[3-(4-AMINOCARBONYL PIPERAZINO AND PIPERIDINO) PROPYL[XANTHINES

The present invention provides xanthine compounds of the formula:

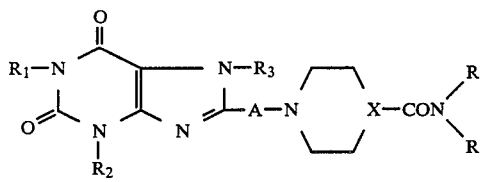

in which:
- $R_1$ is selected from the group consisting of hydrogen and alkyl radicals having from 1 to 5 carbon atoms inclusive, in straight and branched chain;
- $R_2$ is selected from the group consisting of a hydrogen atom, alkyl radicals having from 1 to 5 carbon atoms inclusive, in straight and branched chain, these radicals containing a double bond, and a benzyl radical;
- $R_3$ is selected from the group consisting of a hydrogen atom and a methyl radical;
- A is selected from the group consisting of polymethylene chains $(CH_2)_n$ in which n is an integer from 1 to 4 inclusive, and such chains substituted, when n is higher than 1, by a hydroxy radical;
- X is selected from the group consisting of a nitrogen atom and a

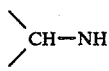

radical; and
the substituents R are each selected from the group consisting of alkyl radicals having from 1 to 5 carbon atoms inclusive, and joined together, they are selected from the group consisting of polymethylene chains having from 4 to 6 carbon atoms, and such chains containing one hereto-atom selected from the group consisting of oxygen and sulfur atoms, in order to form with the nitrogen atom to which they are bonded a heterocyclic radical having one or two hetero-atoms.

The Prior Art in this field may be illustrated by xanthines substituted in 1- or 7-position by an amino-alkyl chain, having coronarodilating (BSM 5086) myocardial anti-ischemic (E.P. 68 544) or anti-allergic (E.P. 21 103) activities. The xanthines of the present invention, substituted in 8-position, surprisingly possess, antispasmodic and psychostimulating properties and crossing the hemo-meningeal barrier, find their therapeutical application as anti-migraine or psychotropic agents.

The present invention also provides a process for preparing a compound of the general formula I characterised in that: a halo compound of the general formula II

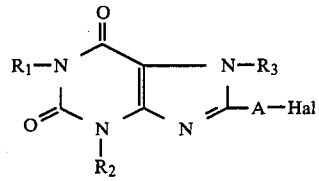

in which $R_1$, $R_2$, $R_3$ and A have the meanings given hereinbefore and Hal represents a chlorine or bromine atom, is condensed with a compound of the general formula III:

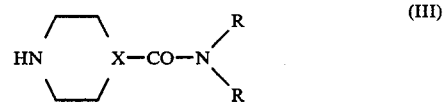

in which X and R have the meanings given hereinbefore.

The condensation is preferably carried out in a solvent selected from alcohols containing up to 4 carbon atoms, such as, for example, methanol, ethanol, propanol or butanol. It is advantageous to carry out the condensation at a temperature between 80° and 110° C. in the presence of an acceptor of the hydrohalic acid, formed during the reaction. This acceptor may be, for example, a tertiary amine such as triethylamine, or an excess of the amine compound of the formula III used for the reaction.

The present invention relates also to a process for the preparation of compounds of the general formula I which is characterised in that an amino compound of the general formula IV:

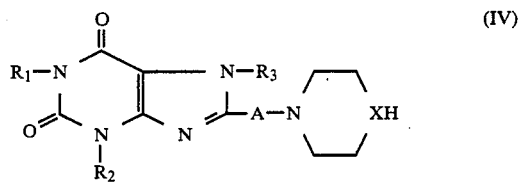

in which $R_1$, $R_2$, $R_3$, A and X have the meanings given hereinbefore, is condensed with a halo compound of the general formula V:

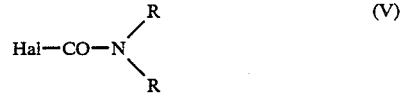

in which R has the meaning given hereinbefore and Hal represents a chlorine or bromine atom.

It is especially advantageous to carry out the condensation in a solvent such as, for example, tetrahydrofuran, dioxan or pyridine, at a temperature between 20° and 60° C., in the presence of a hydracid acceptor formed during the reaction. As acceptor there may be used, for example, triethylamine or pyridine.

The new compounds (I) obtained in this manner may be converted into acid addition salts, these salts also forming part of the present invention. As acids which can be used for the formation of such salts there may be mentioned, for example, in the mineral series hydrochloric, hydrobromic, sulfuric and phosphoric acids, and in the organic series, acetic, propionic, maleic, fumaric, tartaric, citric, oxalic, benzoic, methanesulfonic and isethionic acids.

The new compounds (I) can be purified by physical methods such as crystallisation or chromatography or by chemical methods such as the formation of acid addition salts and decomposition of these salts by means of alkaline agents.

The starting materials of the general formula II and III may be prepared in accordance with the techniques described in French Patent Application No. 82.13.155 filed on 28th July 1982.

The starting materials of the general formula IV may be prepared by debenzylating, by means of hydrogen in the presence of palladium-on-carbon under pressure, corresponding benzyl compounds which may themselves be prepared in accordance with French Patent Application No. 82.13.155 of July 28th 1982.

The compounds of the general formula I and the physiologically tolerable salts thereof have valuable therapeutic and pharmacological properties, especially anti-migraine and central psychotonic properties.

The compounds studied have a spasmolytic activity demonstrated in vitro on isolated preparation of taenia coli in guinea pigs (FERRARI M. and CARPENEDO F., Arch. Int. Pharmacol (1968) 174, 223). The compounds inhibit the contraction which accompanies the depolarisation of the membrane caused by $K^+$ ions and the contraction caused by the extracellular $Ca^{++}$. The mean effective doses ($ED_{50}$) vary, depending on the products, from $2 \times 10^{-5}M$ to $8 \times 10^{-4}M$.

On the other hand, the compounds of the invention inhibit the enzymatic activity of the phosphodiesterase responsible for the degradation of cyclic 3',5'-adenosine monophosphate. The intracellular accumulation of this substance may also explain the relaxation of the smooth muscle fibres. When the enzyme source is crushed rat's brain, the mean inhibiting concentration ($IC_{50}$) is between $1.5 \times 10^{-5}M$ and $1 \times 10^{-4}M$ (NAIR K. G., Biochem (1966), 5, 150). Under the same experimental conditions, theophylline has an $IC_{50}$ of $1.2 \times 10^{-4}M$.

The compounds (I) are of low toxicity; their mean lethal dose ($LD_{50}$) is greater than 800 mg/kg per os.

Furthermore, they have a stimulating effect on the central nervous system from a dose of 50 mg/kg per os administered to guinea pigs. An analgesic effect (according to the heating plate method, WOOLFE G. and McDONALD A. D., J.P.E.T. (1944) 80, 300) could be observed in NMRI mice weighing 26 g after the oral administration of certain compounds (I) at a dosage of 50 mg/kg. This activity has also been demonstrated by the test with phenylbenzoquinone in CD mice. At a dose of 50 mg/kg per os, the compounds of the general formula I have an analgesic activity greater than, or equal to, that of aspirin.

These analgesic properties, together with the effects on the contraction of smooth fibres, permit the use of the compounds of the general formula I the treatment of migraine, especially during the initial period which involves a vaso-constriction phase.

Owing to their central psychotonic activity, the compounds of the invention may also be used in the treatment of asthenia.

The present invention relates also to pharmaceutical compositions containing as active ingredient a compounds of the general formula I or one of its physiologically tolerable salts, in admixture or conjunction with an appropriate pharmaceutical excipient.

The pharmaceutical compositions obtained in this manner are advantageously presented in various forms such as, for example, in the form of compressed tablets, dragées, gelatin-coated pills, glossettes or galenical preparations appropriate for sublingual administration, suppositories, injectable or drinkable solutions, or in a form adapted for administration by aerosol.

The following Examples, which are in no way limiting, illustrate the invention. The melting points, unless specified to the contrary, were determined with a Kofler heating plate.

EXAMPLE 1

1,3,7-trimethyl-8-[3-(4-diethylaminocarbonyl-piperazino)-propyl]-xanthine.

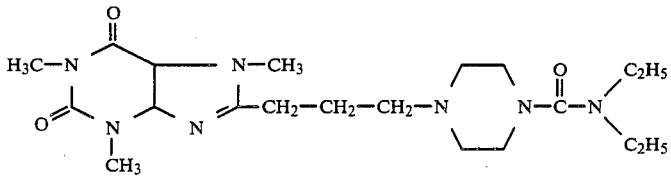

FIRST METHOD

A solution of 21.1 g of 1,3,7-trimethyl-8-(3-bromopropyl)-xanthine, which melts at 130° C., and of 24.7 g of 1-diethylaminocarbonylpiperazine (b.p. 0.15 mm Hg=116°-122° C.) in 530 ml of ethanol is refluxed for 20 hours. Subsequently, the solvent is evaporated under reduced pressure and the residue is taken up in 200 ml of 10% $NaHCO_3$ and 200 ml of $CH_2Cl_2$. The organic solution is decanted and dried over magnesium sulfate. The solvent is evaporated and the mixture is purified by flash chromatography over 1200 g of silica (0.063-0.2) using a mixture of $CH_2Cl_2/CH_3OH$ (92.5/7.5) as eluant. After evaporation of the eluate, 17.3 g of 1,3,7-trimethyl-8-[3-(4-diethylaminocarbonylpiperazino)-propyl]-xanthine are obtained in the form of cream-white crystals melting at 112° C.

The starting materials used in this process may be prepared essentially in accordance with the techniques described in French Patent Application No. 82.13155 of July 28th 1982.

SECOND METHOD

Over a period of 15 minutes at a temperature of 10° C., 3.5 g of diethylcarbamoyl chloride are added to a solution of 8 g of 1,3,7-trimethyl-8-(3-piperazinopropyl)-xanthine (oil) in 100 ml of anhydrous tetrahydrofuran containing 2.5 g of triethylamine. After one hour at room temperature the mixture is heated for 1 hour at 50° C., then cooled, and the solvent is evaporated under reduced pressure. The residue is treated as in the first method. 7 g of 1,3,7-trimethyl-8-[3-(4-diethylaminocarbonylpiperazino)-propyl]-xanthine crystals which melt at 112° C. are obtained.

The starting material 1,3,7-trimethyl-8-(3-piperazinopropyl)-xanthine may be prepared by debenzylating by hydrogen in the presence of palladium-on-carbon, under a pressure of approximately $3 \times 10^6$ Pa, 1,3,7-trimethyl-8-[3-(4-benzylpiperazino)-propyl]-xanthine, which may itself be prepared as described in French Patent Application No. 82.13.155 of 28th July 1982.

EXAMPLES 2 TO 15

The following compounds were prepared in accordance with the methods described in Example 1:

(2) 1,7-dimethyl-3-isobutyl-8-[3-(4-diethylaminocarbonylpiperazino)-propyl]-xanthine, m.p.: 118° C. (methylene chloride).

(3) 1,7-dimethyl-3-n-propyl-8-[3-(4-diethylaminocarbonylpiperazino)-propyl]-xanthine, m.p. of the corresponding fumarate: 161° C. (n-propanol/ether).

(4) 1-ethyl-3-isobutyl-7-methyl-8-[3-(4-diethylaminocarbonylpiperazino)-propyl]-xanthine, m.p.: 101° C. (methylene chloride).

(5) 1-methyl-3-isobutyl-8-(4-diethylaminocarbonylpiperazinomethyl)-xanthine, of which the hydrochloride is an amorphous product.

(6) 1,3-dimethyl-8-[2-(4-diethylaminocarbonylpiperazino)-ethyl]-xanthine, m.p. (capillary): 152°-153° C. (methylene chloride).

(7) 1,3,7-trimethyl-8-[2-(4-diethylaminocarbonylpiperazino)-ethyl]-xanthine, m.p. (capillary) of the corresponding difumarate: 185°-186° C. (n-propanol/ether).

(8) 1,3-dimethyl-8-[3-(4-diethylaminocarbonylpiperazino)-propyl]-xanthine, m.p.: 177° C. (methylene chloride).

(9) 3-benzyl-8-[2-(4-diethylaminocarbonylpiperazino)-ethyl]-xanthine, m.p.: 170° C. (ethyl acetate).

(10) 1,3,7-trimethyl-8-[3-(4-piperidinocarbonylpiperazino)-propyl]-xanthine, m.p.: 152° C. (ethanol).

(11) 1,3,7-trimethyl-8-[3-(4-morpholinocarbonylpiperazino)-propyl]-xanthine, m.p.: 162° C. (methylene chloride).

(12) 1,3,7-trimethyl-8-[3-(4-diethylaminocarbonylaminopiperidino)-propyl]-xanthine, m.p.: 156° C. (methylene chloride).

(13) 3,7-dimethyl-8-[2-(4-diethylaminocarbonylpiperazino)-1-hydroxyethyl]-xanthine.

(14) 1,3,7-trimethyl-8-[2-(4-diethylaminocarbonylpiperazino)-1-hydroxyethyl]-xanthine.

(15) 3,7-dimethyl-8-[2-(4-diethylaminocarbonylpiperazino)-ethyl]-xanthine.

The starting materials used for the synthesis of the compounds above, other than those described in French Patent Application No. 82.13.155 of July 28th 1982, now French Pat. No. 2,531,085, issued Nov. 11, 1984 are the following:

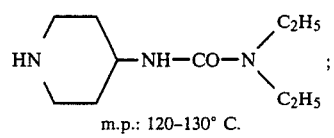

m.p.: 120–130° C.

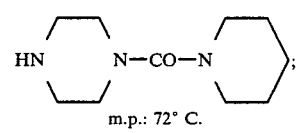

m.p.: 72° C.

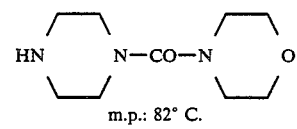

m.p.: 82° C.

and the compounds of the formula

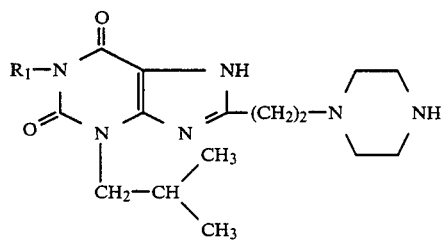

$R_1$=H, m.p. (capillary) of the dihydrochloride: 194°–198° C.

$R_1$=$CH_3$, m.p. (capillary) of the dihydrochloride: 165°–175° C.

prepared by debenzylation of corresponding benzyl compounds under hydrogen, in the presence of palladium-on-carbon under a pressure of $10^7$ Pa.

We claim:

1. A compound selected from the group consisting of xanthine compounds of the formula:

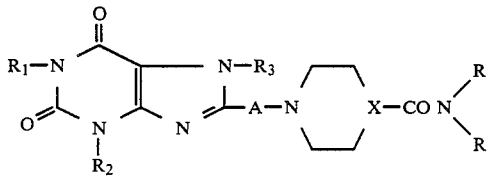

in which:

$R_1$ is selected from the group consisting of hydrogen and ($C_1$–$C_5$) alkyl, in straight and branched chain;

$R_2$ is selected from the group consisting of hydrogen, ($C_1$–$C_5$) alkyl radicals in straight and branched chain and these radicals having a double bond, and benzyl;

$R_3$ is selected from the group consisting of hydrogen and methyl;

A is selected from the group consisting of polymethylene chains $(CH_2)_n$ in which n is an integer from 1 to 4 inclusive, and such chains substituted, when n is higher than 1, by hydroxy;

X is selected from the group consisting of nitrogen and

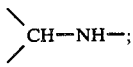

the substituents R are each selected from the group consisting of alkyl radicals having from 1 to 5 carbon atoms inclusive or are joined together in order to form with the nitrogen atom to which they are bonded a piperidino or morpholino radical; and, physiologically tolerable acid addition salts thereof.

2. A compound of claim 1 which is: 1,3,7-trimethyl-8-[3-(4-diethylamino-carbonyl piperazino)propyl]xanthine.

3. A compound of claim 1 which is: 1,7-dimethyl-3 isobutyl-8-[3-(4-diethylamino-carbonyl piperazino)-propyl]xanthine.

4. A compound of claim 1 which is: 1,3,7-trimethyl-8-[3-(4-diethylamino-carbonylamino piperidino)propyl]xanthine.

5. Pharmaceutical compositions suitable for treating migraine containing as active ingredient a compound of claim 1 together with a suitable pharmaceutical carrier.

6. A method for treating a living animal body afflicted with migraine comprising the step of administering to the said living animal an amount of a compound of claim 1 which is effective for the alleviation of the said condition.

7. A compound of claim 1 which is: 1,3,7-trimethyl-8-[3-(4-piperidinocarbonylpiperazino)-propyl]-xanthine.

8. A compound of claim 1 which is: 1,3,7-trimethyl-8-[3-(4-morpholinocarbonylaminopiperazino)-propyl]-xanthine.

* * * * *